United States Patent
Hirouchi et al.

(10) Patent No.: US 11,840,714 B2
(45) Date of Patent: Dec. 12, 2023

(54) ENRICHING DHA IN GLYCERIDE FRACTIONS

(71) Applicant: Nissui Corporation, Tokyo (JP)

(72) Inventors: Yuuji Hirouchi, Tokyo (JP); Isao Yamazaki, Tokyo (JP); Natsuko Watanabe, Tokyo (JP); Kiyomi Furihata, Tokyo (JP)

(73) Assignee: Nissui Corporation, Tokyo (JP)

(*) Notice: Subject to any disclaimer, the term of this patent is extended or adjusted under 35 U.S.C. 154(b) by 156 days.

(21) Appl. No.: 17/273,140

(22) PCT Filed: Sep. 4, 2019

(86) PCT No.: PCT/JP2019/034728
§ 371 (c)(1),
(2) Date: Mar. 3, 2021

(87) PCT Pub. No.: WO2020/050303
PCT Pub. Date: Mar. 12, 2020

(65) Prior Publication Data
US 2022/0106617 A1    Apr. 7, 2022

(30) Foreign Application Priority Data

Sep. 4, 2018 (JP) ............................... 2018-165448

(51) Int. Cl.
| | | |
|---|---|---|
| *C12P 7/6434* | (2022.01) | |
| *C12P 7/6472* | (2022.01) | |
| *C12P 7/6427* | (2022.01) | |
| *C12P 7/6432* | (2022.01) | |

(52) U.S. Cl.
CPC ........... *C12P 7/6434* (2022.01); *C12P 7/6427* (2013.01); *C12P 7/6432* (2022.01); *C12P 7/6472* (2013.01)

(58) Field of Classification Search
None
See application file for complete search history.

(56) References Cited

U.S. PATENT DOCUMENTS

| | | |
|---|---|---|
| 9,029,584 B2 | 5/2015 | Doisaki et al. |
| 2009/0176284 A1 | 7/2009 | Furihata et al. |
| 2010/0190220 A1 | 7/2010 | Furihata et al. |
| 2013/0123525 A1 | 5/2013 | Ikemoto et al. |
| 2018/0051304 A1 | 2/2018 | Kobayashi et al. |
| 2022/0106617 A1* | 4/2022 | Hirouchi ............... C12P 7/6472 |

FOREIGN PATENT DOCUMENTS

| | | |
|---|---|---|
| CN | 108239578 A | 7/2018 |
| JP | 58-165796 A | 9/1983 |
| JP | 03-019694 A | 1/1991 |
| JP | 07-051075 A | 2/1995 |
| JP | 07-268382 A | 10/1995 |
| JP | 08-214892 A | 8/1996 |
| JP | 2004-208546 A | 7/2004 |
| JP | 2017-073980 A | 4/2017 |
| JP | 2017-079650 A | 5/2017 |
| WO | WO-98/18952 A1 | 5/1998 |
| WO | WO-2007/119811 A1 | 10/2007 |
| WO | WO-2009/017102 A1 | 2/2009 |
| WO | WO-2009/040676 A2 | 4/2009 |
| WO | WO-2011/149040 A1 | 12/2011 |
| WO | WO-2012/087153 A1 | 6/2012 |
| WO | WO-2012/118173 A1 | 9/2012 |
| WO | WO-2016/153065 A1 | 9/2016 |
| WO | WO-2017/197453 A1 | 11/2017 |
| WO | WO-2018/116297 A1 | 6/2018 |

OTHER PUBLICATIONS

Pizarro et al., "Influence of different immobilization techniques for Candida cylindracea lipase on its stability and fish oil hydrolysis," Journal of Molecular Catalysis B: Enzymatic, 2012, 78:111-118.

Devos et al., "Enzymatic hydrolysis of phospholipids from Isochrysis galbana for docosahexaenoic acid enrichment," Enzyme and Microbial Technology, Aug. 2, 2006, 39(4):548-554.

Kimura et al., "Application of Immobilized Lipase to Hydrolysis of Triacylglyceride," European Journal of Applied Microbiology and Biotechnology, Mar. 1, 1983, 17(12):107-112.

Adachi et al., "Acidolysis of Sardine Oil by Lipase to Concentrate Eicosapentaenoic and Docosahexaenoic Acids in Glycerides," Journal of Fermentation and Bioengineering, 1993, 75(4):259-264.

Halldorsson et al., "Lipase selectivity toward fatty acids commonly found in fish oil," Eur. J. Lipid Sci. Technol., 2004, 106:79-87.

International Search Report dated Dec. 3, 2019 in PCT/JP2019/034728.

International Search Report dated Nov. 26, 2019 in PCT/JP2019/034729, in Japanese and English.

Pinsirodom et al., "Critical Temperature for Production of MAG by Esterification of Different FA with Glycerol Using Penicillium camembertii Lipase," JAOCS, 2004, 81(6):543-547.

* cited by examiner

*Primary Examiner* — Hope A Robinson
(74) *Attorney, Agent, or Firm* — Foley & Lardner LLP

(57) ABSTRACT

The present invention provides a method of producing a composition containing docosahexaenoic acid as a constituent fatty acid of glycerides. The method includes hydrolyzing a feedstock oil containing glycerides, the glycerides including docosahexaenoic acid as a constituent fatty acid, by action of a first lipase and a second lipase, to increase the proportion of docosahexaenoic acid in glyceride fractions. The first lipase is at least one lipase selected from the group consisting of a lipase obtained from a microorganism of the genus *Thermomyces*, a lipase obtained from a microorganism of the genus *Pseudomonas*, a lipase obtained from a microorganism of the genus *Burkholderia*, and a lipase obtained from a microorganism of the genus *Alcaligenes*. The second lipase is a partial glyceride lipase.

8 Claims, 3 Drawing Sheets

ENRICHING DHA IN GLYCERIDE FRACTIONS

CROSS-REFERENCE TO RELATED APPLICATIONS

This application is the U.S. National Stage of PCT/JP2019/034728, filed Sep. 4, 2019, which claims priority to JP 2018-165448, filed Sep. 4, 2018.

TECHNICAL FIELD

The present invention relates to a method of producing highly unsaturated fatty acid containing glycerides by making use of lipase hydrolysis reaction.

BACKGROUND ART

Highly unsaturated fatty acids are nutrients that are essential for the growth of vertebrates including the human and in recent years, many reports have been made with regard to their involvement in cardiovascular and inflammatory diseases. In particular, the intake of n-3 highly unsaturated fatty acids such as docosahexaenoic acid (DHA) and eicosapentaenoic acid (EPA) has been found to be useful for human health, as reported in many publications. A report has also been published to show the importance of the ratio betweeen the intake levels of n-3 and n-6 highly unsaturated fatty acids. Modern society is characterized by the tendency that the energy intake level as well as the intake levels of saturated fatty acids and n-6 highly unsaturated fatty acids are increasing whereas the intake level of n-3 highly unsaturated fatty acids is decreasing, and this tendency has been considered to be associated with various kinds of lifestyle diseases.

Fish oils are oils or fats that are rich in n-3 highly unsaturated fatty acids and their intake is widely recommended; what is more, in order to ensure that n-3 highly unsaturated fatty acids are taken in more efficiently, measures for enriching n-3 highly unsaturated fatty acids in fish oils are being studied. One of such measures is lipase reaction based enrichment of highly unsaturated fatty acids.

Lipases are enzymes that catalyze the reaction by which oils and fats are hydrolyzed to free fatty acids and glycerol and it is known that various animals and plants as well as microorganisms possess lipases. Certain types of lipases do not equally act on all fatty acids and their reactivity differs with such factors as the binding position on glycerides, the carbon chain length of fatty acids and the number of double bonds they have. Those lipases can therefore be used for selective hydrolysis of fatty acids and, as the result, it is possible to enrich particular fatty acids in glyceride fractions. To give an example, the technique of enriching highly unsaturated fatty acids in glyceride fractions by means of a lipase derived from *Candida cylindracea* has been known from a long time ago (PTL 1).

This lipase-assisted hydrolysis reaction is an effective method for enrichment of highly unsaturated fatty acids. The more hydrolyzed are fatty acids other than the highly unsaturated fatty acids of interest, the more enriched are the highly unsaturated fatty acids in glyceride fractions.

It has also been reported for the method of enriching highly unsaturated fatty acids in glyceride fractions by means of lipase-assisted hydrolysis reaction that by carrying out the hydrolysis reaction at low temperatures not higher than 25° C., the proportion of saturated fatty acids in glyceride fractions can be lowered (PTL 2).

Methods of using two types of lipase in combination to enrich highly unsaturated fatty acids in glyceride fractions have also been reported. For example, PTL 3 discloses that by using two types of lipase in combination as selected from *Candida cylindracea* derived lipase, *Rhizopus* derived lipase, and *Chromobacterium* lipase, glycerides are obtained that have a higher DHA content than in the case where the respective lipases are used independently. What is more, PTL 4 discloses that by using *Mucor miehei* derived lipase, *Candida cylindracea* derived lipase or *Rhizopus oryzae* derived lipase in combination with *Penicillium camenberti* derived lipase, DHA is enriched in glyceride fractions with improved selectivity, thereby producing oils or fats that contain highly unsaturated fatty acids at an increased ratio of DHA to EPA.

On the other hand, lipase may be used not to enrich DHA in glyceride fractions but to produce free fatty acids that contain DHA at high concentrations and such methods have also been reported. For example, PTL 5 discloses a method in which highly unsaturated fatty acids are first enriched in glycerides by means of a lipase acting on triglycerides and then hydrolysis is carried out using the lipase acting on triglycerides together with a partial glyceride lipase to thereby obtain a composition that contains DHA as a free fatty acid at high concentration. Furthermore, PTL 6 discloses a method in which a lipase derived from the genus *Alcaligenes* that preferentially hydrolyzes sn-1,3 position on triglycerides is used in combination with a partial glyceride lipase to perform hydrolysis, thereby obtaining free fatty acids containing DHA at high concentration.

CITATION LIST

Patent Literature

PTL 1: JP S58-165796 A
PTL 2: WO 2011/149040
PTL 3: JP H7-268382 A
PTL 4: WO 98/18952
PTL 5: JP 2004-208546 A
PTL 6: JP 2017-73980 A

SUMMARY OF INVENTION

Technical Problem

The present invention aims at providing a novel means that employs a plurality of lipases in combination for enriching DHA in glyceride fractions.

Solution to Problem

The present inventors conducted an intensive study with a view to attaining the above-stated object and found, as the result, that by using a particular lipase for enriching docosahexaenoic acid in glycerides in combination with a partial glyceride lipase, whereby the DHA concentration in glyceride fractions can be considerably increased over the case where the particular lipase is used independently. As mentioned above, lipases derived from *Candida cylindracea* and other microorganisms have been used for the purpose of enriching DHA in glyceride fractions. The DHA concentration can be increased if the hydrolysis reaction is carried out a plurality of times but lipases with which the DHA concentration in glyceride fractions can be consistently increased to an adequate level by a single run of hydrolysis reaction are limited.

Based on the above-mentioned finding, the present inventors continued their study and eventually accomplished the present invention.

Briefly, the present invention may be summarized as follows.

[1] A method of producing a composition containing docosahexaenoic acid as a constituent fatty acid of glycerides, comprising:
   hydrolyzing a feedstock oil containing glycerides comprising docosahexaenoic acid as a constituent fatty acid by action of a first lipase and a second lipase, thereby increasing the proportion of docosahexaenoic acid in glyceride fractions,
   wherein the first lipase is at least one lipase selected from the group consisting of a lipase derived from a microorganism of the genus *Thermomyces*, a lipase derived from a microorganism of the genus *Pseudomonas*, a lipase derived from a microorganism of the genus *Burkholderia*, and a lipase derived from a microorganism of the genus *Alcaligenes*, and
   wherein the second lipase is a partial glyceride lipase.

[2]. The method as recited in [1], wherein the microorganism of the genus *Thermomyces* is *Thermomyces lanuginosus*, the microorganism of the genus *Pseudomonas* is *Pseudomonas fluorescens*, the microorganism of the genus *Burkholderia* is *Burkholderia cepacia*, and the microorganism of the genus *Alcaligenes* is *Alcaligenes* sp.

[3] The method as recited in [1] or [2], wherein the partial glyceride lipase is a lipase derived from a microorganism of the genus *Penicillium*.

[4]. The method as recited in [3], wherein the microorganism of the genus *Penicillium* is *Penicillium camenberti*.

[5] The method as recited in any one of [1] to [4], wherein the amount in which the second lipase is used ranges from 0.01 to 20 in terms of activity ratio relative to the first lipase which is taken as 1.

[6] The method as recited in any one of [1] to [5], wherein the hydrolysis reaction is terminated at the point in time when the acid value of the reaction solution has come to lie between 90 and 160.

[7] The method as recited in any one of [1] to [6], wherein the hydrolysis reaction is performed at a temperature between 10 and 50° C.

[8] The method as recited in any one of [1] to [7], wherein a third lipase for enriching docosahexaenoic acid which is other than the first lipase is acted upon the feedstock oil either simultaneously with or at a different time from the first and second lipases.

[9] The method as recited in [8], wherein the third lipase is a lipase derived from *Candida cylindracea*.

[10] The method as recited in any one of [1] to [9], which further comprises a step of recovering the glycerides after the reaction.

Advantageous Effects of Invention

According to the present invention, a composition with an increased proportion of DHA in constituent fatty acids of glyceride fractions can be produced using a plurality of lipases together. Notably, if a lipase derived from a microorganism of the genus *Thermomyces* is combined with a lipase derived from a microorganism of the genus *Penicilium*, DHA can be enriched to a level comparable to the case of the *Candida cylindracea* derived lipase which has heretofore been used industrially.

DESCRIPTION OF EMBODIMENTS

Figure 1:
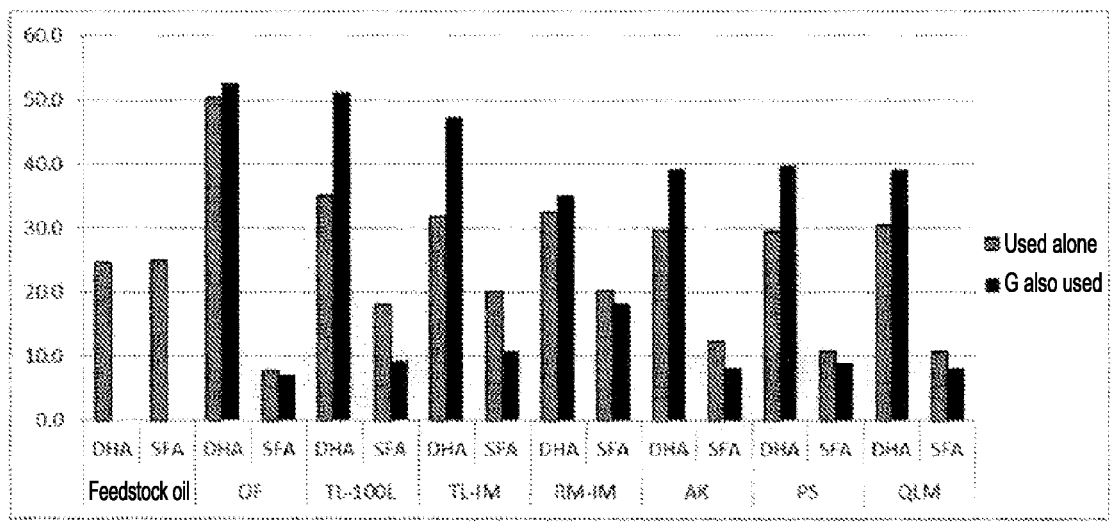
FIG. 1 is a graph showing the proportions of DHA and SFA in glyceride fractions of lipase reaction solutions prepared from deacidified tuna oil by using different types of lipase either independently or in combination with Lipase G.

On the following pages, the present invention will be described more specifically.

In this specification, the following abbreviations are sometimes used.
  DHA: docosahexaenoic acid
  EPA: eicosapentaenoic acid
  MUFA: mono-unsaturated fatty acids
  SFA: saturated fatty acids
  TAG: triacylglycerol or triglyceride
  DAG: diacylglycerol or diglyceride
  MAG: monoacylglycerol or monoglyceride The present invention provides a method of producing a composition containing docosahexaenoic acid as a constituent fatty acid of glycerides, comprising hydrolyzing a feedstock oil containing glyceride comprising docosahexaenoic acid as a constituent fatty acid by action of a first lipase and a second lipase, thereby increasing the proportion of docosahexaenoic acid in glyceride fractions, wherein the first lipase is a lipase for enriching docosahexaenoic acid in glycerides, specifically at least one lipase selected from the group consisting of a lipase derived from a microorganism of the genus *Thermomyces*, a lipase derived from a microorganism of the genus *Pseudomonas*, a lipase derived from a microorganism of the genus *Burkholderia*, and a lipase derived from a microorganism of the genus *Alcaligenes*, and wherein the second lipase is a partial glyceride lipase (the method is hereinafter sometimes referred to as the production method of the present invention).

As used herein, the term "highly unsaturated fatty acids" refers to fatty acids containing no less than 18 carbon atoms and no less than 3 double bonds, for example, fatty acids containing no less than 20 carbon atoms and no less than 3 or 4 double bonds, or fatty acids containing no less than 20 carbon atoms and no less than 5 double bonds. Specific examples include α-linolenic acid (18:3, n-3), γ-linolenic acid (18:3, n-6), dihomo-γ-linolenic acid (20:3, n-6), arachidonic acid (20:4, n-6), eicosapentaenoic acid (20:5, n-3), docosapentaenoic acid (22:5, n-6), docosahexaenoic acid (22:6, n-3), etc. These are known to be abundant in certain kinds of microorganism oils, vegetable oils, and sea creature oils. Specific examples include: sea creature oils as from fish such as sardine, tuna and bonito, crustaceans such as krill, and marine animals such as seals; vegetable oils collected as from perilla, flax, soybean, and rapeseed; oils produced by microorganisms belonging to the genus *Mortierella*, the genus *Penicillium*, the genus *Aspergillus*, the genus *Rhodotorula*, and the genus *Fusarium*.

As used herein, the term "a composition containing docosahexaenoic acid as a constituent fatty acid of glycerides" means a glyceride composition containing glycerides having docosahexaenoic acid bound thereto. Here, the glyceride composition is a composition containing glycerides as main constituents and it may contain glycerides in an amount of, say, no less than 80 mass %, no less than 85 mass %, no less than 90 mass %, no less than 95 mass %, no less than 99 mass %, no less than 99.5 mass %, or no less than 99.9 mass %.

In the present invention, the glycerides include triglycerides, diglycerides, and monoglycerides.

The feedstock oil to be used in the production method of the present invention may be any oil that contains glycerides comprising docosahexaenoic acid as a constituent fatty acid. Docosahexaenoic acid may bind to any of sn-1, sn-2 and sn-3 positions of glycerol. Exemplary feedstock oils include naturally occurring oils that are known to be rich in the above-mentioned highly unsaturated fatty acids and may specifically be exemplified by sea creature oils (such as sardine oil, tuna oil, bonito oil, krill oil, seal oil, etc.), vegetable oils (such as perilla oil, linseed oil, soybean oil, rapeseed oil, etc.), and microorganism oils (such as oils produced by microorganisms belonging to the genus *Mortierella*, the genus *Penicillium*, the genus *Aspergillus*, the genus *Rhodotorula*, and the genus *Fusarium*). It is preferred to select feedstock oils that comprise no less than a certain amount of docosahexaenoic acid in the constituent fatty acids of glycerides; preferred feedstock oils comprise at least 10 area %, or at least 15 area %, and more preferably at least 20 area % of docosahexaenoic acid. While there is no upper limit to the content of docosahexaenoic acid, feedstock oils that inherently have a high content of docosahexaenoic acid often have no great need for enrichment, so a preferred feedstock is such that it contains no greater than 70 area %, or no greater than 65 area %, and more preferaly no greater than 60 area % of docosahexaenoic acid. In other words, it is preferred to use feedstock oils that comprise 10 to 70 area %, 10 to 65 area %, or 15 to 65 area %, more preferably 10 to 60 area %, 15 to 60 area %, or 20 to 60 area % of docosahexaenoic acid. In one embodiment, the feedstock oil to be used in the production method of the present invention is fish oil, preferably tuna oil or bonito oil.

In the present invention, these oils may be used either as such or used after they are processed as by refining or enrichment. In the case of fish oil, for example, a whole fish or remnants of fishery processing such as the head, skin, bones or viscera of fish are ground and steamed, then pressed to be separated into stick water (SW) and pressed meal; the oil or fat that is obtained together with the stick water is separated therefrom by centrifugation, whereupon a crude oil is prepared. The crude oil may be degummed, deacidified, decolored, deodorized or otherwise treated to yield a refined fish oil. To refine the crude oil, thin-film distillation (such as molecular distillation or short-path distillation) or alkali deacidification may be employed. In one embodiment, the feedstock oil to be used in the production method of the present invention is a fish oil treated by short-path distillation, preferably tuna oil treated by short-path distillation.

The first lipase to be used in the present invention is a lipase for enriching docosahexaenoic acid in glyceride fractions and it has such properties that it is less active on docosahexaenoic acid in the constituent fatty acids of glycerides so that the proportion of docosahexaenoic acid in the constituent fatty acids of glyceride fractions is increased after the hydrolysis reaction. It should be noted here that in this specification, increasing the proportion of docosahexaenoic acid in the constituent fatty acids of glyceride fractions may also be referred to as enriching docosahexaenoic acid in glyceride fractions.

Lipases that are capable of enriching docosahexaenoic acid in glycerides and which have the above-mentioned properties are lipases derived from microorganisms of the genus *Alcaligenes* (such as Lipase QLM, Lipase QLC, and Lipase PL, each manufactured by Meito Sangyo Co., Ltd.), lipases derived from microorganisms of the genus *Burkholderia* (such as Lipase PS Amano SD manufactured by Amano Enzyme Inc.), lipases derived from microorganisms of the genus *Pseudomonas*(such as Lipase AK Amano manufactured by Amano Enzyme Inc.), and lipases derived from microorganisms of the genus *Thermomyces* (such as Lipozyme TL 100L or Lipozyme TL IM, as manufactured by Novozymes A/S). These lipases are each on the commercial market and readily available. These may optionally be immobilized before use. If desired, two or more types of lipases may be used in combination.

Lipases derived from microorganisms of the genus *Thermomyces* are preferably lipases derived from *Thermomyces lanuginosus* (such as Lipozyme TL 100L or Lipozyme TL IM). Lipases derived from microorganisms of the genus *Pseudomonas* are preferably lipases derived from *Pseudomonas fluorescens* (such as Lipase AK Amano). Lipases derived from microorganisms of the genus *Burkholderia* are preferably lipases derived from *Burkholderia cepacia* (such as Lipase PS Amano SD). Lipases derived from microorganisms of the genus *Alcaligenes* are preferably lipases derived from *Alcaligenes* sp. (such as Lipase QLM).

The amount of use of the first lipase is not particularly limited but it is preferred that no less than 10 units per gram of the feedstock oil (namely, 10 units/g oil), and no less than 30 units/g oil which takes into account practical feasibility including reaction rate are added to the reaction system. For instance, no less than 100 units/g oil, no less than 200 units/g oil, no less than 400 units/g oil, no less than 800 units/g oil or no less than 1,600 units/g oil may be added to the reaction system. For example, the lipase can be used in an amount of 10 to 2,000 units/g oil, 100 to 1,600 units/g oil, 200 to 1,200 units/g oil, or 300 to 1,000 units/g oil. As for the immobilized lipase, it can be repeatedly used, so unlike the lipase that is not immobilized and which is added in the required amount, an excess of the immobilized lipase may be added to the reaction system, from which it can be recovered after the reaction for repeated use. Hence, at least the amounts of use that are indicated above with respect to one gram of the feedstock oil may be added to the reaction system; they may be changed to reasonable values depending, for example, on whether the immobilized lipase is used in batch treatment or column treatment, or how many times its use is to be repeated. For example, the immobilized lipase may be used in an amount of 3 to 30% (w/w), or 4 to 25% (w/w), more preferably 5 to 20% (w/w), relative to the feedstock oil. In connection with these lipases, one unit of each enzyme is the amount that generates one micromole of free fatty acids per minute and which is measured by the method described in 3. Lipolytic Activity Test under "4.03 Digestion Test" of the General Test, Processes and Apparatus in the Japanese Pharmacopoeia, 17th Edition. Specifically, olive oil as the substrate is mixed with a liquid emulsifier, whereupon it is emulsified to form a substrate solution. After allowing the lipase to act on the olive oil, sodium hydroxide is added to neutralize the generated fatty acids and the remaining excess of sodium hydroxide is titrated with hydrochloric acid. Titration of sodium hydroxide with hydrochloric acid is also performed on a blank solution prepared without adding the lipase. The lipolytic activity of the lipase (in units/g) is determined from the difference between the two values of titration.

The second lipase to be used in the present invention is a partial glyceride lipase. As used herein, the term "partial glyceride lipase" refers to a lipase that hydrolyzes monoglycerides and diglycerides but does not hydrolyze triglycerides as well. Examples of partial glyceride lipases include lipases derived from microorganisms of the genus *Penicillium* (such as Lipase G Amano 50 manufactured by Amano Enzyme Inc.). In one embodiment, the second lipase to be used in the present invention is a lipase derived from microorganisms of the genus *Penicillium*, preferably a lipase derived from *Penicillium camemberti* (such as Lipase G Amano 50).

The amount of use of the second lipase is not particularly limited but it can be no less than 0.01, no less than 0.02, no less than 0.05, no less than 0.1, no less than 0.2, or no less than 0.25 and no more than 20, no more than 10, no more than 4, no more than 2, or no more than 1 in terms of activity ratio (the ratio of unit numbers) relative to the first lipase which is taken as 1. For instance, the second lipase can be used in such amounts that the activity ratio of the first lipase to the second lipase lies between 1:0.01 to 20, 1:0.02 to 10, 1:0.05 to 5, 1:0.1 to 3, 1:0.2 to 2, 1:0.1 to 2, or 1:0.25 to 1.

In this connection, one unit of the partial glyceride lipase shall be the amount of the enzyme that is measured by the LV emulsification method and which causes a one-micromole increase of fatty acids per minute. The LV emulsification method determines unit numbers by the following procedure: the lipase is acted on an emulsion of vinyl laurate and the reaction is quenched by an ethanol/acetone mixed solvent and after neutralizing the generated fatty acids with sodium hydroxide, the remaining sodium hydroxide is titrated with hydrochloric acid to quantify the generated fatty acids.

In the production method of the present invention, the first lipase and the second lipase are acted on the feedstock oil to perform hydrolysis reaction. The first and the second lipase may both be present within the reaction system from the very beginning of the reaction; alternatively, they may be sequentially supplied into the reaction system with a certain interval provided between the two additions. In the latter case, the second lipase is usually added after the addition of the first lipase. Since the first lipase has difficulty in acting on docosahexaenoic acid in the constituent fatty acids of glycerides, the proportion of docosahexaenoic acid in glyceride fractions can be increased by causing the first lipase to act on the feedstock oil. It should be noted here that since the second lipase is a partial glyceride lipase, it does not directly act on the feedstock oil if the feedstock oil does not contain partial glycerides; in the present invention, however, causing a lipase to act on partial glycerides resulting from the feedstock oil is also included in the concept of causing the lipase to act on the feedstock oil.

In a preferred embodiment, the first lipase is a lipase derived from *Thermomyces lanuginosus* (such as Lipozyme TL 100L or Lipozyme TL IM), the second lipase is a lipase derived from *Penicillium camemberti* (such as Lipase G Amano 50), and the activity ratio for the enzymatic amounts of the first and second lipases to be added to the reaction system can lie between 1:0.01 to 20, between 1:0.02 to 10, between 1:0.05 to 5, between 1:0.1 to 3, between 1:0.2 to 2, between 1:0.1 to 2, or between 1:0.25 to 1. By using these lipases in combination, compositions having the proportion of DHA in the constituent fatty acids of glyceride fractions increased to practically feasible levels can consistently be produced by a single run of lipase reaction. As used herein, the term "a single run of lipase reaction" covers not only the case where all lipases that are required are added at the start of the reaction and no other lipase is added during the reaction but also the case where the start of hydrolysis reaction by one lipase is followed by addition of another lipase into the same reaction system.

In addition to the first and second lipases, a third lipase which is other than the first lipase and is capable of DHA enrichment may also be used in the hydrolysis reaction to be performed in the present invention. Even if the third lipase is also used, the effect of using the first and second lipases in combination will not be impaired. In the case of using the third lipase, it may be acted on the feedstock oil either simultaneously with the first or second lipase or with a certain interval provided after their addition. Two or more types of the third lipase may be used.

Examples of the third lipase include lipases derived from the genus *Candida*, preferably a lipase derived from *Candida cylindracea*. The lipase derived from *Candida cylindracea* (also known as *Candida rugosa*) may be exemplified by Lipase OF and Lipase AY Amano 30SD (Amano Enzyme Inc.)

The amount of use of the third lipase is not particularly limited but in terms of activity ratio, it can be no less than 0.02, no less than 0.05, no less than 0.1, no less than 0.2, or no less than 0.25 and no more than 50, no more than 20, no more than 10, no more than 4, no more than 2, or no more than 1 relative to the first lipase which is taken as 1. For instance, the third lipase can be used in such amounts that the activity ratio of the first to the third lipase lies between 1:0.02 to 50, between 1:0.05 to 20, between 1:0.1 to 10, between 1:0.1 to 2, between 1:0.25 to 4, between 1:0.2 to 2, or between 1:0.25 to 1.

Lipase-assisted hydrolysis reaction need be performed in the presence of a sufficient amount of water for the hydrolytic activity of the lipase to develop. The amount of addition of water ranges from 0.1 to 2.5 parts by weight, or from 0.2 to 1.5 parts by weight, preferably from 0.3 to 1 part by weight per part by weight of the feedstock oil.

In order to suppress the deterioration of fatty acids, deactivation of lipases and other deleterious effects, hydrolysis is preferably performed under an inert gas atmosphere such as dry nitrogen. Antioxidants such as tocopherol, ascorbic acid and t-butyl hydroquinone may be contained in the feedstock oil.

The reaction temperature for hydrolysis is not particularly limited as long as lipases exhibit their activity at that temperature; to give examples, it is between 10 to 50° C., preferably between about 10 to 40° C. To lower the proportion of saturated fatty acids in the constituent fatty acids of glyceride fractions, the reaction is usually carried out at no higher than 25° C., preferably between 10 and 25° C., more preferably between 15 and 25° C. Saturated fatty acids tend to be taken excessively in the modern diet. Since the docosahexaenoic acid enriched compositions obtained by the production method of the present invention can be used as raw materials for health foods, medicines and other products, they preferably have low contents of saturated fatty acids. The lower the reaction temperature, the lower the content of saturated fatty acids; however, considering that at 10° C. and below, the very rate of lipase reaction becomes unduly slow and the viscosity of oils or fats becomes high, the most preferred reaction temperature is in the neighborhood of 15 to 25° C. In the case of high-volume reaction, it may be carried out with the temperature in the reaction vessel being set between 15 and 25° C. on average while ensuring that changes in the reaction temperature will be held within the range of about ±5° C. Hydrolysis reaction can be performed under flowing conditions created by mechanical agitation or with an inert gas or other media being blown in.

Hydrolysis reaction should be continued until the proportion of docosahexaenoic acid that occupies the constituent fatty acids of glyceride fractions becomes an intended level. The reaction conditions can differ with such factors as the feedstock oil and the amount of enzyme. For example, in the case where the first lipase is used in a large amount, the reaction time may be shortened and in the case where it is used in a small amount, the reaction time may be prolonged. In one embodiment, the reaction time can, for example, be no less than 5 hours, no less than 6 hours, no less than 7 hours, no less than 8 hours, no less than 9 hours, or no less than 10 hours, and no more than 24 hours, no more than 20 hours, no more than 18 hours, no more than 16 hours, no more than 15 hours, no more than 14 hours, no more than 13 hours, no more than 12 hours, or no more than 11 hours. For example, in the case where tuna oil (DHA content ~23%) or the like is used as the feedstock oil, the reaction time is preferably 7 hours or longer. Usually, by subjecting the feedstock oil to hydrolysis reaction for 5 to 24 hours, the proportion of docosahexaenoic acid can be increased to 35 area % and above by a single run of lipase reaction. In one embodiment, the production method of the present invention ensures that the proportion of docosahexaenoic acid in glyceride fractions can be increased to 35 area % and above, 40 area % and above, 45 area % and above, 46 area % and above, 47 area % and above, 48 area % and above, 49 area % and above, 50 area % and above, or 51 area % and above by a single run of lipase reaction.

In this specification, unless otherwise noted, the proportion (area %) of docosahexaenoic acid in glyceride fractions is determined as follows: glycerides in the oil layer of the lipase reaction product are methyl esterified by the sodium methylate method and, thereafter, the free fatty acids generated by the lipase reaction are removed and the residue is subjected to measurement by gas chromatography to give values (peak areas), based on which the proportion (area %) of docosahexaenoic acid in glyceride fractions is calculated. The conditions for gas chromatographic analysis are as follows.

Device type: Agilent 6890N GC system (Agilent Technologies)
Column: DB-WAX J&W 122-7032
Column temperature: Held at 180° C. for 0 minutes, then elevated from 180° C. to 230° C. at
3° C./min, and held for 15 minutes.
Injection temperature: 250° C.
Injection method: Splitting
Split ratio: 30:1
Detector temperature: 250° C.
Detector: FID
Carrier gas: Helium (1 mL/min, constant flow)

If necessary, acid value (AV) may also be used as an indicator for the degree of hydrolysis. In the present invention, acid value is a numeric value measured by a method as modified from the JOCS Standard Methods for the Analysis of Fats, Oils and Related Materials (2013 Edition) (compiled by Japan Oil Chemists' Society). Specifically, acid value is measured in the following manner: about 100 mg of a sample is dissolved in 20 mL of a neutral solvent (ethanol: diethyl ether=1:1 v/v) and after adding a phenolphthalein solution, neutralizing titration is performed with a 0.1 M potassium hydroxide standard solution and the acid value of interest is computed by the following formula:

AV=amount of titrant (mL)×56.11×factor of potassium hydroxide standard solution/sample weight (g)×(1/10).

In the above formula, "factor of potassium hydroxide standard solution" means "(standardization determined) true concentration of the standard solution divided by the indicated concentration of the prepared standard solution)."

In the present invention, hydrolysis reaction is usually performed to give an acid value of 90 to 160, whereby the proportion of docosahexaenoic acid in the constituent fatty acids of glyceride fractions can be adequately increased. If the reaction continues until the acid value exceeds 160, the percent recovery of docosahexaenoic acid is likely to decrease. Hence, in the production method of the present invention, hydrolysis reaction can be terminated at the point in time when the acid value of the reaction solution has come to lie between 90 and 160, or between 100 and 150, or between 110 and 140.

By performing hydrolysis as described above, a mixture of unreacted triglycerides and the hydrolysate can be obtained as the reaction solution. The first lipase has difficulty hydrolyzing the ester linkage between glycerol and docosahexaenoic acid and, hence, as hydrolysis proceeds, the proportion of docosahexaenoic acid that occupies the constituent fatty acids of glycerides in the reaction solution will increase. Upon termination of hydrolysis, the proportion of docosahexaenoic acid in the constituent fatty acids of glyceride fractions will be no less than 35 area %, say, no less than 40 area %, no less than 45 area %, no less than 46 area %, no less than 47 area %, no less than 48 area %, no less than 49 area %, no less than 50 area %, or no less than 51 area %. On the other hand, free fatty acids will mostly be occupied by fatty acids other than docosahexaenoic acid.

The production method of the present invention may further comprise the step of recovering glycerides after the lipase-assisted hydrolysis reaction. The composition obtained as the result has a higher proportion of docosahexaenoic acid in the constituent fatty acids of glyceride fractions than the feedstock oil does. To recover the glycerides, the following procedure may be followed: after the period of hydrolysis reaction ends, the lipases used are deactivated by heating or adding an acid, and the aqueous layer, free fattty acids and glycerol are removed from the reaction solution. The aqueous layer, free fattty acids and glycerol can be removed by known methods. For example, after the period of hydrolysis reaction ends, the lipases used are deactivated by adding an acid; the aqueous layer comprising the lipases and glycerol is removed from the reaction solution as by centrifugation; further, rinsing with water is repeated until the aqueous layer becomes neutral; thereafter, free fatty acids are removed from the resulting oil layer. Free fatty acids can be separated and removed by known methods, for example, removing them in the form of alkali salts, using a liquid chromatographic apparatus, or removing them by distillation; preferred methods are the removal of free fatty acids in the form of alkali salts, and removal by distillation such as molecular distillation or short-path distillation. By removing the free fatty acids, a triglyceride/ partial glyceride mixture containing docosahexaenoic acid at high concentration is obtained.

The compositions obtained by the produciton method of the present invention have high proportions of triglerides in glyceride fractions as compared with the case where lipases are used individually. For example, the proportion of triglycerdies in the glycerides recovered in the produciton method of the present invention is no less than 70 area %, no less than 75 area %, no less than 80 area %, or no less than 85 area %. Consequently, according to the present invention, the recovered glycerides need not be subjected to further removal of partial glycerides and this helps simplify the refining process.

The recovered glycerides can be further subjected to deacidifying, decoloring or deodorizing treatment. Deacidifying, decoloring or deodorizing treatment may be performed by any methods; the deacidifying treatment may be exemplified by distillation treatment, the decoloring treatment may be exemplified by treatment as with activated clay, activated charcoal, or silica gel, and the deodorizing treatment may be exemplified by steam distillation. If the deacidifying treatment is performed by distllation, monoglycerides are also removed simultaneously and this contributes to further increasing the ratio of triglycerides in the oil obtained.

EXAMPLES

The present invention is now described more specifically by means of the following Examples, to which the present invention is by no means limited.

Unless otherwise noted, the values indicated by % in the following Examples are % by weight.

In each of the Examples, the composition of fatty acids, the acid value, and the composition of lipids were measured by the following methods.

In the present invention, area % is the proportion to total peak area of the peak area of each of the components in a chart of analysis conducted by gas chromatography or thin-layer chromatograph/hydrogen flame ionization detector (TLC/FID) on a mixture of glycerides that are composed of various fatty acids; in other words, area % indicates the ratio of the content of the component represented by the peak. The composition of fatty acids was computed from the results obtained by gas chromatographic analysis in accordance with the method described in the Examples; the composition of lipids was computed from the results of analysis using TLC/FID.

<Measuring the Composition of Fatty Acids>

The composition of fatty acids in a feedstock fish oil was measured by gas chromatography after methyl esterification of the fish oil. To be specific, 1 mL of 1 N sodium methylate/methanol solution was added to 40 µL of fish oil and the resulting mixture was stirred at 80° C. for one minute. Subsequently, 1 mL of 1 N hydrochloric acid was added to neutralize the mixture, to which 2 mL of hexane and 3 mL of a saturated aqueous solution of sodium chloride were added and stirred; after allowing the stirred mixture to settle undisturbed, the upper layer was subjected to measurement by gas chromatography.

The fatty acid composition of the glyceride fractions of an oil subjected to lipase reaction was measured by a process consisting of methyl esterifying the glyceride fractions, removing the free fatty acids generated by lipase reaction, and subjecting the residue to gas chromatography. To be specific, 1 mL of 1 N sodium methylate/methanol solution was added to 70 µL of the reaction solution and the resulting mixture was stirred at 80° C. for one minute. Subsequently, 1 mL of 1 N hydrochloric acid was added to neutralize the mixture, to which 700 µL of hexane and 3 mL of a saturated aqueous solution of sodium chloride were added and stirred; after allowing the stirred mixture to settle undisturbed, the upper layer containing methyl ester and free fatty acids was recovered. The operation of removing free fatty acids from the obtained upper layer was performed as described below. To 700 µL of the hexane solution which was the recovered upper layer having the methyl ester and free fatty acids dissolved therein, 10-20 µL of triethylamine was added and mixed under shaking; thereafter, the entire volume of the mixture was loaded on a solid-phase extraction cartridge (Agilent Technology, BOND ELUT SI, 100 mg, 1 mL) and the methyl ester was eluted with 1 mL of a mixed solution of hexane and ethyl acetate (hexane: ethyl acetate=50:1 in volume ratio) to remove the free fatty acids. The residue was subjected to measurement by gas chromatography.

Conditions for Gas Chromatographic Analysis

Device type: Agilent 6890N GC system (Agilent Technologies)

Column: DB-WAX J&W 122-7032

Column temperature: Held at 180° C. for 0 minutes, then elevated from 180° C. to 230° C. at 3° C./min, and held for 15 minutes.

Injection temperature: 250° C.

Injection method: Splitting

Split ratio: 30:1

Detector temperature: 250° C.

Detector: FID

Carrier gas: Helium (1 mL/min, constant flow)

<Measurement of Acid value (AV)>

Acid value (AV) was measured by a method as modified from the JOCS Standard Methods for the Analysis of Fats, Oils and Related Materials (2013 Edition) (compiled by Japan Oil Chemists' Society). Specifically, about 100 mg of a sample was dissolved in 20 mL of a neutral solvent (ethanol: diethyl ether=1:1 in volume ratio) and after adding a phenolphthalein solution, neutralizing titration was performed with a 0.1 M potassium hydroxide standard solution and the acid value of interest was computed by the following formula:

$$AV = \text{amount of titrant (mL)} \times 56.11 \times \text{factor of potassium hydroxide standard solution/sample weight (g)} \times (1/10).$$

<Measuring the Composition of Lipids>

The composition of lipids was measured by thin-layer chromatograph/hydrogen flame ionization detector (TLC/FID, IATROSCAN, Mitsubishi Kagaku Iatron, Inc.). Specifically, 20 μL of an oil was dissolved in 1 mL of hexane and 0.5 μL of the solution was loaded on a Chromarod. A thin layer was developed for 30 minutes using a mixed solution of hexane, diethyl ether, and acetic acid (hexane:diethyl ether:acetic acid=70:30:1 in volume ratio) as a developing solvent. The developed thin layer was analyzed by IATROSCAN.

Example 1

<Feedstock Oil>

Sterols and fatty acids were removed from rinsed crude tuna oil by short-path distillation to prepare a deacidified tuna oil (DHA=24.6%) which was used as a feedstock oil.

<Lipases>

The following lipases were used.
Lipase PS Amano SD (herein also referred to as Lipase PS; Amano Enzyme Inc.)
Lipase AK Amano (herein also referred to as Lipase AK; Amano Enzyme Inc.)
Lipase OF (Meito Sangyo Co., Ltd.)
Lipozyme TL 100L (Novozymes Japan Co., Ltd.)
Lipozyme TL IM (Novozymes Japan Co., Ltd.)
Lipozyme RM IM (Novozymes Japan Co., Ltd.)
Lipase QLM (Meito Sangyo Co., Ltd.)
Lipase G Amano 50 (herein also referred to as Lipase G, Amano Enzyme Inc.)

<Preparation of Lipase Reaction Solutions>

For the reaction using a single lipase alone, 3 g of deacidified tuna oil was mixed with water and each of the lipases listed in Table 1 and the mixture was subjected to reaction at 18° C. (measured value: 18.8° C.) for the periods of time also shown in Table 1. After the reaction, 85% phosphoric acid was added in 1.5% relative to the oil and the mixture was stirred at 18° C. for an hour to deactivate the lipase. Subsequently, the mixture was rinsed with hot water three times to obtain a lipase reaction solution.

For the reaction using a first lipase in combination with Lipase G, Lipase G was added to the reaction system in such an amount that its activity would be a quarter of the activity of the first lipases listed in Table 1 (i.e., 200 units/g oil when it was combined with Lipase OF, and 250 units/g oil when it was combined with the other lipases) and lipase reaction solutions were prepared by repeating the same procedure as that employed in the above-mentioned case of using a single lipase alone.

<Results>

The proportions of DHA and SFA (area %) in the glyceride fractions of the obtained lipase reaction solutions are shown in FIG. 1. In the case where Lipase OF or Lipozyme RM IM was used in combination with Lipase G, the proportion of DHA increased only slightly. On the other hand, in the case where Lipase PS, Lipase AK, Lipozyme TL 100L, Lipozyme TL IM or Lipase QLM was used in combination with Lipase G, the proportion of DHA was shown to increase considerably. Such effect of the combined use was particularly marked in Lipozyme TL 100L and Lipozyme TL IM.

Example 2

Lipase reaction solutions were prepared as in Example 1, except that the mixing ratio of Lipozyme TL 100L to Lipase G was adjusted to 4:0, 4:1, 4:2, or 4:4 in terms of activity ratio. The reaction time was set for 20 hours. Note that in the case where the mixing ratio was 4:2 and 4:4, the reaction temperature was 15° C. Lipozyme TL 100L was used in an amount of 100, 200, 400, 800 or 1,600 units/g oil.

Figure 2:
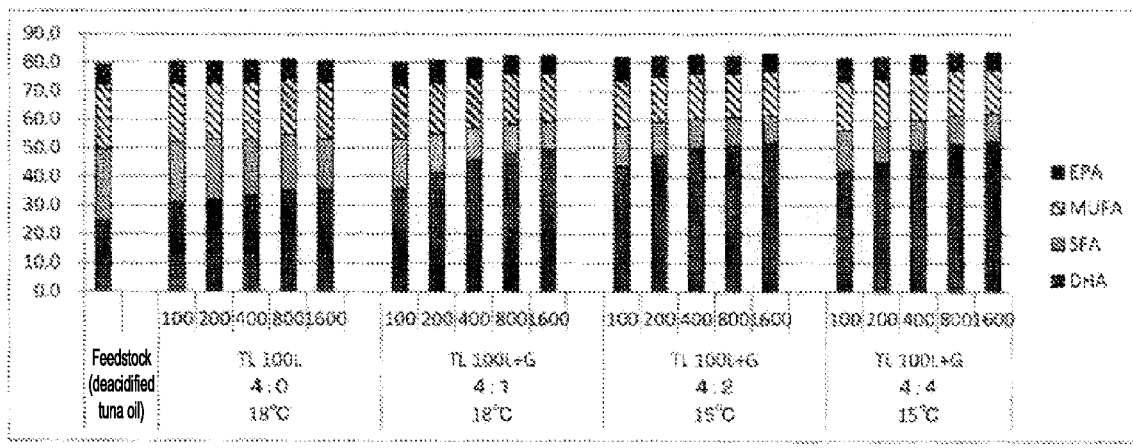
FIG. 2 is a graph showing the proportions of DHA, EPA, MUFA and SFA in glyceride fractions of lipase reaction solutions prepared from deacidified tuna oil by using Lipozyme TL 100L and Lipase Gin combination.

The proportions (area %) of DHA, EPA, MUFA and SFA in the glyceride fractions of the obtained lipase reaction solutions are shown in Table 2 and FIG. 2. By additionally using Lypase G, the proportion of DHA could be increased considerably as compared with the case where Lipozyme TL 100L was used alone. In particular, when the mixing ratio of Lipozyme TL 100L to Lipase G was adjusted to 4:2 or 4:4 and Lipozyme TL 100L was used in an amount of 800 units/g oil or more, the proportion of DHA reached 51 area % and above by a single run of lipase hydrolysis reaction. In contrast, Lipozyme TL 100L alone did not increase the proportion of DHA considerably even when it was used in increased amounts.

The combined use of Lipozyme TL 100L and Lipase G could also increase the proportion (area %) of triglycerides in the glyceride fractions (Table 2).

TABLE 1

| Origin | Name of enzyme | Water:Oil (w/w) | Amouont of enzyme | Temperature | Reaction time |
|---|---|---|---|---|---|
| genus *Burkholderia* | Lipase PS | 2:1 | 1000 unit/g oil | 18° C. | 20 hr |
| genus *Pseudomonas* | Lipase AK | 2:1 | 1000 unit/g oil | | 20 hr |
| genus *Candida* | Lipase OF | 3:2 | 800 unit/g oil | | 24 hr |
| genus *Thermomyces* | Lipozyme TL 100 L | 2:1 | 1000 unit/g oil | | 20 hr |
| genus *Thermomyces* | Lipozyme TL IM | 2:1 | 5% relative to oil | | 20 hr |
| genus *Rhizomucor* | Lipozyme RM IM | 2:1 | 5% relative to oil | | 20 hr |
| genus *Alcaligenes* | Lypase QLM | 2:1 | 1000 unit/g oil | | 20 hr |

TABLE 2

| | Feedstock oil (deacidified tuna oil) | TL 100 L (4:0) 18° C. Amount of TL 100 L used (unit/oil) | | | | | TL 100 L + G (4:1) 18° C. | | | | |
|---|---|---|---|---|---|---|---|---|---|---|---|
| | | 100 | 200 | 400 | 800 | 1600 | 100 | 200 | 400 | 800 | 1600 |
| DHA | 24.6 | 31.4 | 32.2 | 33.5 | 35.0 | 35.8 | 35.9 | 41.3 | 45.8 | 48.3 | 48.7 |
| SFA | 24.9 | 21.1 | 20.9 | 19.9 | 19.8 | 17.6 | 17.2 | 13.7 | 11.2 | 10.2 | 9.6 |
| MUFA | 22.9 | 20.2 | 19.8 | 19.8 | 19.3 | 19.9 | 18.9 | 18.0 | 17.6 | 17.4 | 16.9 |
| EPA | 6.8 | 7.6 | 7.4 | 7.3 | 6.9 | 7.1 | 8.0 | 7.6 | 6.8 | 6.4 | 6.2 |
| TAG | | 68.0 | 71.1 | 59.7 | 62.4 | 63.1 | 79.1 | 84.0 | 77.7 | 79.7 | 79.7 |
| DAG | | 29.6 | 28.9 | 38.0 | 35.9 | 34.9 | 20.7 | 16.0 | 21.8 | 20.1 | 18.9 |
| MAG | | 2.4 | 0.0 | 2.2 | 1.6 | 2.0 | 0.1 | 0.0 | 0.2 | 0.3 | 0.4 |
| Acid value | | 39.6 | 47.3 | 55.1 | 69.3 | 73.7 | 88.7 | 85.6 | 103.7 | 117.1 | 133.1 |

| | TL 100 L + G (4:2) 15° C. Amount of TL 100 L used (unit/oil) | | | | | TL 100 L + G (4:4) 15° C. | | | | |
|---|---|---|---|---|---|---|---|---|---|---|
| | 100 | 200 | 400 | 800 | 1600 | 100 | 200 | 400 | 800 | 1600 |
| DHA | 43.4 | 47.6 | 50.0 | 51.0 | 51.6 | 42.0 | 44.9 | 49.3 | 51.5 | 52.3 |
| SFA | 13.8 | 11.4 | 10.4 | 9.8 | 8.7 | 14.4 | 12.7 | 10.6 | 9.9 | 9.7 |
| MUFA | 16.6 | 16.1 | 15.7 | 15.3 | 15.6 | 17.0 | 16.7 | 16.3 | 15.8 | 15.5 |
| EPA | 7.7 | 7.0 | 6.4 | 6.1 | 6.1 | 7.8 | 7.3 | 6.5 | 6.1 | 6.0 |
| TAG | 85.3 | 87.7 | 87.1 | 83.7 | 81.8 | 83.2 | 87.9 | 82.8 | 83.5 | 81.9 |
| DAG | 14.5 | 12.2 | 12.6 | 16.0 | 17.6 | 16.7 | 12.1 | 17.0 | 18.2 | 17.8 |
| IMAG | 0.3 | 0.1 | 0.3 | 0.3 | 0.6 | 0.1 | 0.0 | 0.3 | 0.3 | 0.5 |
| Acid value | 84.7 | 102.6 | 116.6 | 137.0 | 150.0 | 86.6 | 99.1 | 115.8 | 128.5 | 144.4 |

Example 3

Lipase reaction solutions were prepared as in Example 1, except that the mixing ratio of Lipozyme TL 100L to Lipase G was adjusted to 4:1 in terms of activity ratio and that the reaction temperature was set to 18° C. or 39° C. Lipozyme TL 100L was used in an amount of 100, 200, 400, 800 or 1,600 units/g oil.

Figure 3:
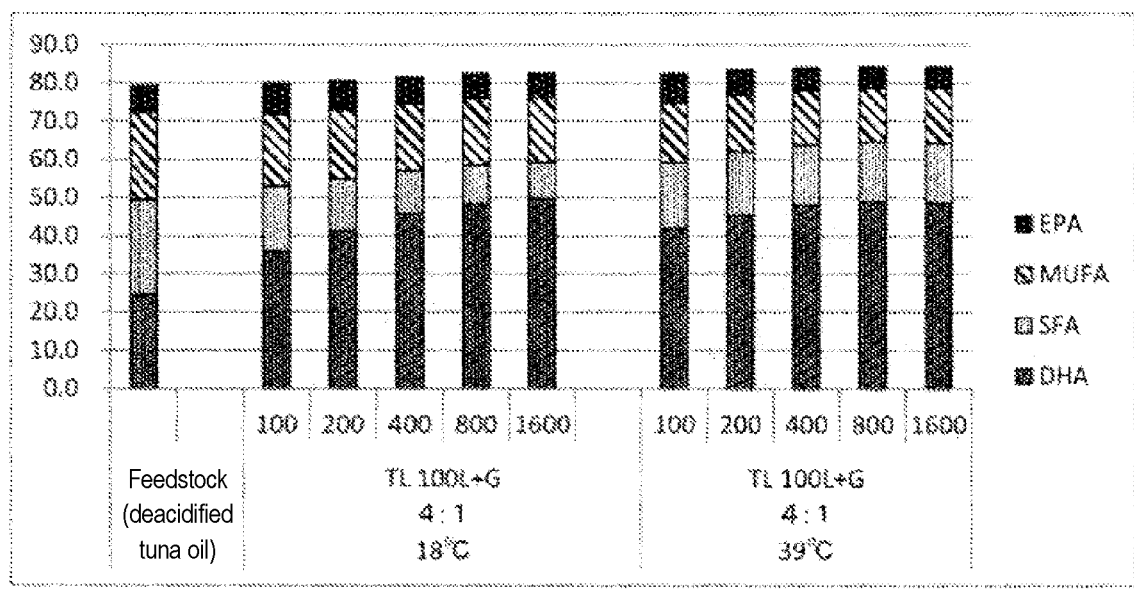
FIG. 3 is a graph showing the proportions of DHA, EPA, MUFA and SFA in glyceride fractions of lipase reaction solutions prepared from deacidified tuna oil by using Lipozyme TL 100L and Lipase Gin combination at a reaction temperature of 18° C. or 39° C.

The proportions (area %) of DHA, EPA, MUFA and SFA in the glyceride fractions of the obtained lipase reaction solutions are shown in FIG. 3. The combined use of TL 100L and Lipase G allowed the proportion of DHA to increase considerably in both cases where the reaction temperature was 18° C. and 39° C.

Example 4

Lipase reaction solutions were prepared as in Example 1, except that the mixing ratio of Lipozyme TL 100L, Lipase G and Lipase AY was adjusted to 4:1:1 or 4:1:4 in terms of activity ratio and that the reaction temperature was set to lie between 15° C. and 16° C. Lipozyme TL 100L was used in an amount of 100, 200, 400, 800 or 1,600 units/g oil.

Figure 4:
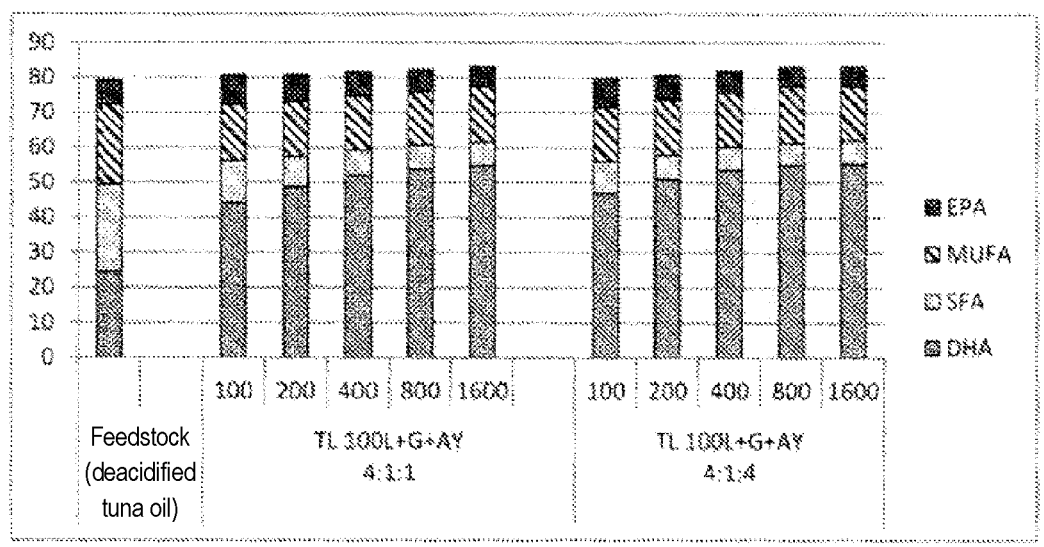
FIG. 4 is a graph showing the proportions of DHA, EPA, MUFA and SFA in glyceride fractions of lipase reaction solutions prepared from deacidified tuna oil by using Lipozyme TL 100L, Lipase G and Lipase AY in combination.

The proportions (area %) of DHA, EPA, MUFA and SFA in the glyceride fractions of the obtained lipase reaction solutions are shown in FIG. 4. By adding Lipase AY to Lipozyme TL 100L and Lipase G, the proportion of DHA in the glyceride fractions could be further increased.

Example 5

Figure 5:
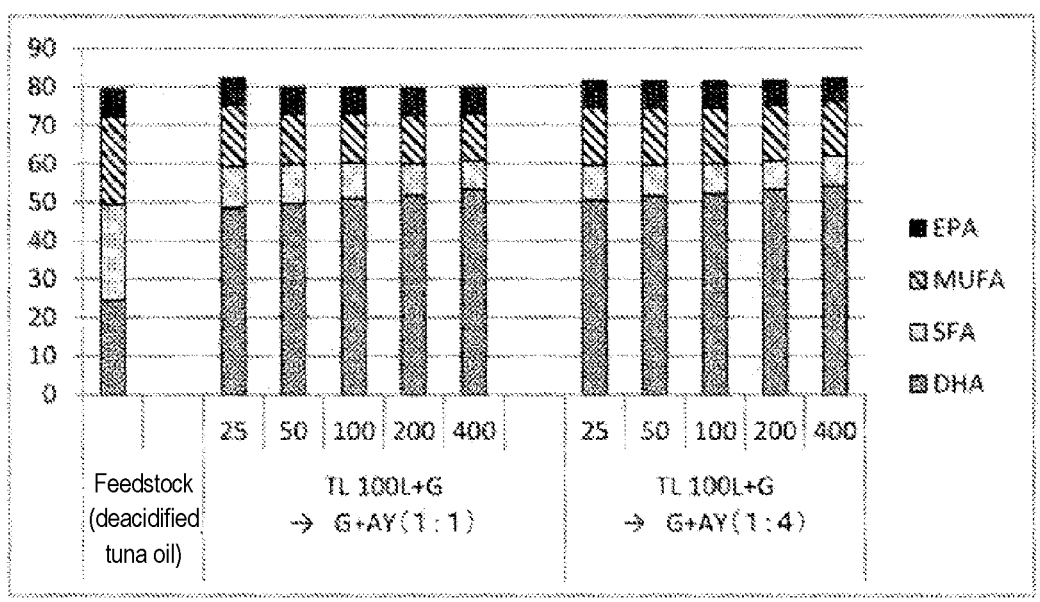
FIG. 5 is a graph showing the proportions of DHA, EPA, MUFA and SFA in glyceride fractions of lipase reaction solutions obtained by first performing reaction using Lipozyme TL 100L and Lipase Gin combination, and then performing reaction using Lipase G and Lipase AY in combination.

Using Lipozyme TL 100L (400 units/g) and Lipase G (100 units/g), reaction was carried out at a reaction temperature of 15-16° C. for 20 hours; thereafter, Lipase G in the amounts shown in FIG. 5 (i.e., 25-400 units/g) and an equal amount (1:1) or four times higher amount (1:4) of Lipase AY were additionally supplied and reaction was carried out at a reaction temperature of 17° C. for 8 hours.

The proportions (area %) of DHA, EPA, MUFA and SFA in the glyceride fractions of the obtained lipase reaction solutions are shown in FIG. 5. When the reaction using Lipozyme TL 100L and Lipase G was followed by a short duration of the reaction using Lipase G or Lipase AY, the proportion of DHA in the glyceride fractions could be further increased.

INDUSTRIAL APPLICABILITY

In accordance with the present invention, for the purpose of enriching docosahexaenoic acid in glyceride fractions, a plurality of lipases that are not hihgly effective on their own are used in combination, whereby compositions containing docosahexaenoic acid as a constituent fatty acid of glycerides can be produced. Said compositions can be used as raw materials for health foods, medicines and other products.

The invention claimed is:

1. A method of producing a composition containing docosahexaenoic acid (DHA), comprising:
    hydrolyzing a feedstock oil comprising glycerides having DHA as a constituent fatty acid, by reacting the feedstock oil with a first lipase and a second lipase to form a reaction solution, and
    recovering the glycerides having DHA as a constituent fatty acid after reaction;
    wherein the hydrolyzing increases proportions of DHA in the reaction solution,
    wherein the first lipase is at least one lipase selected from the group consisting of:
        a lipase obtained from a microorganism of the genus *Thermomyces*,
        a lipase obtained from a microorganism of the genus *Pseudomonas*,
        a lipase obtained from a microorganism of the genus *Burkholderia*, and
        a lipase obtained from a microorganism of the genus *Alcaligenes*, wherein the second lipase is a partial glyceride lipase; and wherein hydrolyzing is terminated at a point in time when the acid value of the reaction solution is between 90 and 160.

2. The method of claim 1, wherein the microorganism of the genus *Thermomyces* is *Thermomyces lanuginosus*, the microorganism of the genus *Pseudomonas* is *Pseudomonas fluorescens*, the microorganism of the genus *Burkholderia* is *Burkholderia cepacia*, and the microorganism of the genus *Alcaligenes* is *Alcaligenes* sp.

3. The method of claim 1, wherein the partial glyceride lipase is a lipase obtained from a microorganism of the genus *Penicillium*.

4. The method of claim 3, wherein the microorganism of the genus *Penicillium* is *Penicillium camemberti*.

5. The method of claim 1, wherein the second lipase ranges from 0.01 to 20 in terms of activity ratio relative to the first lipase.

6. The method of claim 1, wherein the hydrolyzing is performed at a temperature between 10 and 50° C.

7. The method of claim 1, further comprising hydrolyzing the feedstock oil by reacting with a third lipase for enriching docosahexaenoic acid in the feedstock oil either simultaneously with or at a different time from the first and second lipases.

8. The method of claim 7, wherein the third lipase is a lipase obtained from *Candida cylindracea*.

* * * * *